United States Patent [19]

Lambert

[11] Patent Number: 4,494,544
[45] Date of Patent: Jan. 22, 1985

[54] RELAY FOR A HEART DEFIBRILLATOR

[75] Inventor: Willibrordus J. S. Lambert, Eindhoven, Netherlands

[73] Assignee: Honeywell Inc., Minneapolis, Minn.

[21] Appl. No.: 197,365

[22] Filed: Oct. 15, 1980

Related U.S. Application Data

[63] Continuation of Ser. No. 077,424, Sep. 20, 1979, abandoned.

[30] Foreign Application Priority Data

Sep. 27, 1978 [NL] Netherlands .......................... 7809766

[51] Int. Cl.³ .............................................. H61R 1/30
[52] U.S. Cl. ................................................ 128/419 D
[58] Field of Search ......................... 315/15, 46, 55, 57, 315/181, 189, 190, 196, 200, 203, 219, 220, 261, 262, 272, 276, 279; 128/419 D; 335/228, 272

[56] References Cited

U.S. PATENT DOCUMENTS

| | | | |
|---|---|---|---|
| 2,426,068 | 8/1947 | Taviaferro | 335/200 |
| 2,872,628 | 2/1959 | Buchtewkirch | 335/261 |
| 2,943,170 | 6/1960 | Vradenburgh | 335/200 |
| 3,541,484 | 11/1970 | DeLucia | 335/196 |

*Primary Examiner*—William E. Kamm
*Attorney, Agent, or Firm*—Mitchell J. Halista

[57] ABSTRACT

A heart defibrillator in which the relay which connects the high voltage capacitor to the electrodes comprises a switching arm which is mounted on a pivotable armature and the free end of which accommodates a movable contact which co-operates with a fixed contact which comprises a contact face which encloses an angle of between 5° and 30° with the movement direction of the movable contact. The armature has an axial play which is so large that, when the relay is energized, it occupies a first axial position against the force of a spring. The contacts are then pressed one against the other. When the relay is deenergized, the armature is moved to a second axial position by the spring. The contacts are clear of each other in this second axial position. The switching arm is formed by a strip of fibre-glass reinforced epoxy resin, the smallest dimension of which extends perpendicularly to the movement direction of the movable contact.

5 Claims, 3 Drawing Figures

U.S. Patent   Jan. 22, 1985   4,494,544
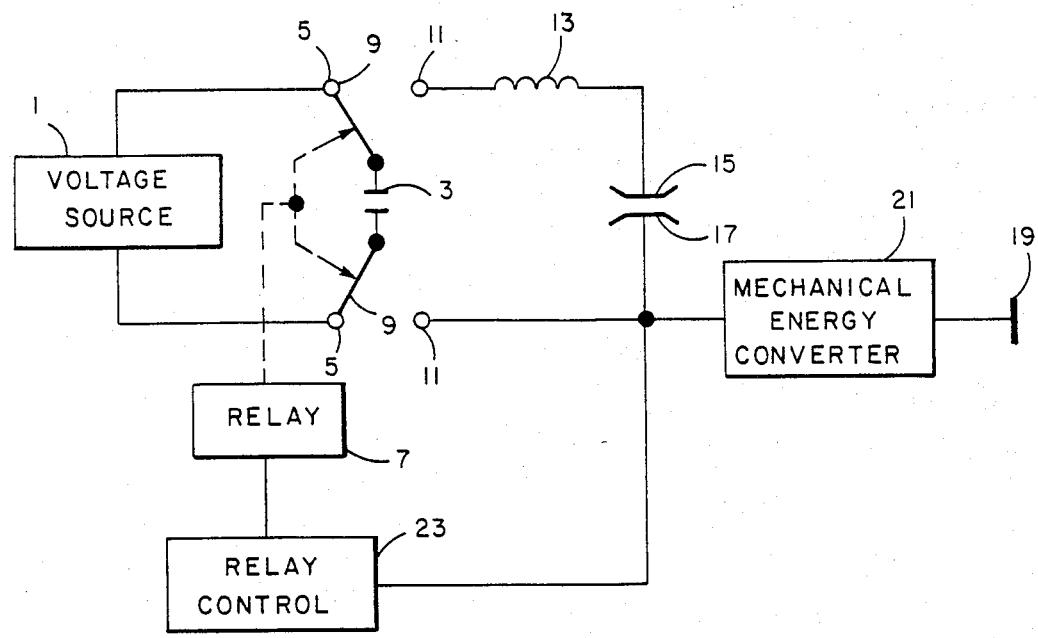
FIG. 1
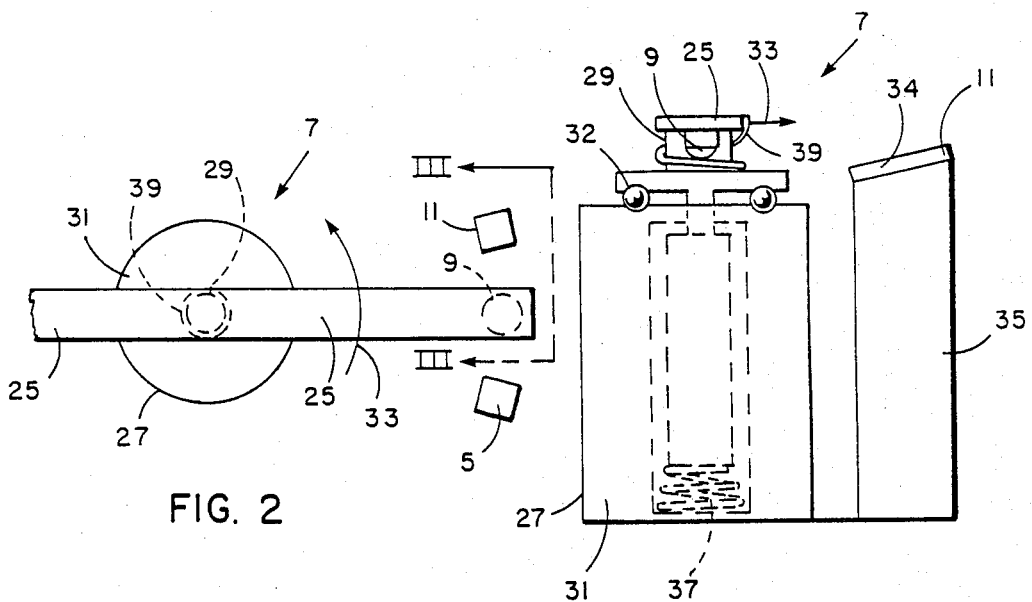
FIG. 2
FIG. 3

RELAY FOR A HEART DEFIBRILLATOR

The present application is a continuation of application Ser. No. 077,424, filed Sept. 20, 1979, now abandoned.

The invention relates to a heart defibrillator, comprising a high voltage capacitor which is to be charged by means of a voltage source and which can be connected, via at least one relay, to two electrodes which are to be arranged on the body of a patient, said relay comprising a pivotable armature on which a switching arm is secured, the free end of which accommodates a movable contact which co-operates with a fixed contact which comprises a contact face which encloses an angle of between 5° and 30° with the movement direction of the movable contact.

A device of this kind is known from U.S. Pat. No. 3,525,957. During use of the defibrillator, the relay contacts must carry a very large current (for example 55A) during a brief period of time (for example, 6 ms). Because of the very high voltage of the capacitor in the charged condition and the safety requirements imposed on a patient circuit, the relay should satisfy a number of severe requirements. One of these requirements consists in that in the open condition a large creepage path and air gap must exist between the contacts, so that no leakage currents can flow to the patient. This implies that the switching path is comparatively long. A second requirement consists in that no or substantially no bouncing of the relay is permissible when the contacts close, because this would have adverse effects on the shape of the defibrillation pulse. A third requirement consists in that the switching time must be less than 20 ms in order to enable synchronization of the defibrillation pulse with the electrocardiogram (ECG).

Even though the known relay can be constructed to satisfy these requirements, the fixed and movable contacts are pressed together with a comparatively high force so that the friction is high therebetween. Therefore, when the relay is switched off and notably when the contact faces are burnt to some extent, there is a risk of sticking of the contacts.

The invention has for its object to provide a relay of the described kind in which the risk of sticking is virtually eliminated.

To this end, the heart defibrillator in accordance with the invention is characterized in that the armature has an axial play which is so large that, when the relay is energized, the armature occupies a first axial position, against the force of a spring, in which the movable contact is pressed against the fixed contact whilst, when the energizing of the relay is terminated, the armature is placed in a second axial position by the spring in which the movable contact is clear of the fixed contact, the switching arm being formed by a strip of glass-fibre reinforced epoxy resin and its smallest dimension extending perpendicularly to the movement direction of the movable contact.

Glass-fibre reinforced epoxy resin is a comparatively rigid material. Thus, the spring force required for interrupting the intimate contact between the fixed and movable contact is achieved with a comparatively short spring path, so that the axial play of the armature may be small.

As a result, the relay returns to its starting position substantially without friction or sticking of the contacts after termination of energizing of the relay.

The invention will be described in detail hereinafter with reference to the accompanying diagrammatic drawing.

FIG. 1 shows an electrical circuit diagram of a heart defibrillator.

FIG. 2 is a plan view of an embodiment of a relay used in a heart defibrillator in accordance with the invention, and FIG. 3 is a side elevation at an increased scale of a part of the same relay.

FIG. 1 diagrammatically shows a heart defibrillator of the type described in U.S. Pat. No. 3,913,588. The heart defibrillator comprises a voltage source 1 for generating a high direct voltage of, for example, 5 kV for charging a capacitor 3 of, for example, 32 μF. To this end, the voltage source 1 is connected to a set of fixed contacts 5 of a double-pole relay 7, the movable contacts 9 of which, contacting the fixed contacts 5 in the rest position as shown, are connected to the capacitor 3. One contact of the second set of fixed contacts 11 of the relay 7 is connected, via a coil 13, to a first electrode 15, whilst the second contact is connected directly to a second electrode 17. The relay 7 can be energized by operation of a push-button 19 whih activates a control circuit 23 via a mechano-electrical energy converter 21. When this takes place, the capacitor 3 is connected to the electrodes 15, 17 arranged on the body of a patient, so that it is discharged via the heart of the patient.

FIGS. 2 and 3 show an embodiment of the relay 7. The relay comprises two switching arms 25, only one of which is fully shown for the sake of simplicity. These switching arms are driven by a known rotary magnet 27 which is formed by an armature 29 which co-operates with a coil 31 and whose linear movement is converted into a rotary movement by means of a ball track (not shown). An example of such a rotary magnet is the "Ledex rotary solenoid" from Ledex Inc., Dayton, Ohio, U.S.A. which is described in U.S. Pat. Nos. 3,264,530 and 4,157,521.

When the coil 31 is energized, the switching arm 25 moves in the direction of the arrow 33. The movable contact 9 is arranged on the free end of the switching arm 25. The fixed contact 11 is constructed as a flat plate having a contact face 34 which is mounted on a support 35, so that the contact face encloses an angle of between 5° and 30° (preferably approximately 15°) with respect to the rotational movement direction 33 of the movable contact 9. The fixed contact 11 may also have another shape: for example, it may be integral with the support 35. The fixed contact 11 as well as the movable contact 9 is preferably made of tungsten which is capable of resisting large currents and intense sparking. The other fixed cotact 5 may be constructed in the same way as the fixed contact 11. However, this is not necessary, because the requirements imposed thereon are less severe.

The switching arm 25 is made of a strip of glass-fibre reinforced epoxy resin. It is mounted on the armature 29 so that its smallest dimension extends perpendicularly to the movement direction, with the result that the movable contact 9 is slightly resilient in the direction perpendicular to the rotational movement direction 33.

The long switching path and the high speed at which the movable contact 9 approaches the fixed contact 11 could cause a serious bouncing effect, if the contact face of the fixed contact were not arranged at an angle of from 5° to 30° with respect to the movement direction in the described manner. In the described situation, the movable contact runs upwards against the slope formed by the contact face 34, so that the speed at which the two parts 9, 11 collide is comparatively low. After the movable contact 9 has come to a standstill, it contacts the fixed contact 11 under a comparatively high contact pressure which is inter alia due to the resilience of the switching arm 23. Bouncing is minimized by the large force exerted on the movable contact 9 in the vertical direction and by the low speed of collision. Tests of the described relay have demonstrated that the relay bounced only once for at the most 0.2 ms.

After the current through the coil 31 has been switched off, the movable contact 9 is released from the fixed contact 11 by means of a compression spring 37 (denoted by a broken line) which displaces the armature 29 in the vertical direction, utilizing the axial play of the armature 29. After disengagement of the movable contact, the switching arm is returned to its rest position by means of a reset spring 39, the movable contact 9 then contacting the fixed contact 5 again.

Instead of the prescribed relay comprising two fixed contacts 5, 11 per movable contact 9, use can also be made of a relay comprising only contact pairs 9–11, one or two separate relays being provided for the charging of the capacitor. The described two-armed relay can also be replaced by two one-armed relays.

What is claimed is:

1. A relay for a heart defibrillator comprising:
   relay coil means for actuating the relay;
   pivotable armature means which rotates to a first rotational position from a second rotational position when the relay coil means is energized and which further moves axially to a first axial position from a second axial position when the relay coil means is energized;
   spring means for forcing the armature to the second axial position when the relay coil means is not energized;
   a switching arm secured to the armature means for rotation and axial movement therewith, comprising a strip of electrically non-conductive rigid material and having a smallest dimension oriented perpendicular to the plane of rotation of the arm;
   a movable contact disposed on an end of the arm which is remote from the armature for movement therewith; and a fixed contact disposed to engage a moveable contact when the relay is energized and having a contact face which encloses an angle between 5° and 30° in the direction of rotational movement of the moveable contact;
   wherein the armature has sufficient axial movement between the first and second axial positions so that when the relay coil means is energized and the armature is in the first rotational position and the first axial position, the moveable contact is pressed against the fixed contact, while when energizing of the relay coil means is terminated the armature moves to the second axial position and the movable contact is clear of the fixed contact.

2. A relay as claimed in claim 1, wherein the contacts comprise tungsten.

3. A relay as set forth in claim 1 wherein said strip of material is a glass-fibre reinforced epoxy resin.

4. A relay as set forth in claim 3 and further including a second spring means for forcing the armature to the second rotational position when the relay coil means is not energized.

5. A relay for a heart defibrillator comprising:
   relay coil means for actuating the relay;
   privotable armature means which rotates to a first rotational position from a second rotational position when the relay coil means is energized and which further moves axially to a first axial position from a second axial position when the relay coil means is energized;
   spring means for forcing the armature to the second axial position when the relay coil means is not energized;
   a switching arm secured to the armature means for rotation and axial movement therewith, comprising a strip of electrically non-conductive rigid material and having a smallest dimension oriented perpendicular to the plane of rotation of the arm;
   a movable contact disposed on an end of the arm which is remote from the armature for movement therewith; and a fixed contact disposed to engage a movable contact when the relay is energized and having a contact face which encloses an angle between 5° and 30° in the direction of rotational movement of the moveable contact;
   wherein the armature has sufficient axial movement between the first and second axial positions so that when the relay coil means is energized and the armature is in the first rotational position and the first axial position, the moveable contact is pressed against the fixed contact, while when energizing of the relay coil means is terminated the armature moves to the second axial position and the movable contact is clear of the fixed contact and wherein said pivotable armature means includes a ball track having a pair of inner facing surfaces inclined to the plane of rotation of said armature means and a ball in said track between said surfaces and arranged to roll along said inner surfaces to induce said rotation and axial movement of said pivotable means when said coil means is energized.

* * * * *